(12) United States Patent
Komuro et al.

(10) Patent No.: US 7,557,230 B2
(45) Date of Patent: Jul. 7, 2009

(54) LATENT CURING AGENT

(75) Inventors: Katsuhiko Komuro, Tochigi (JP); Tadasu Kawashima, Tochigi (JP); Masahiko Ito, Tochigi (JP); Daisuke Masuko, Tochigi (JP)

(73) Assignees: Sony Corporation, Tokyo (JP); Sony Chemical & Information Device Corporation, Tokyo (JP)

( * ) Notice: Subject to any disclaimer, the term of this patent is extended or adjusted under 35 U.S.C. 154(b) by 171 days.

(21) Appl. No.: 11/884,527

(22) PCT Filed: Jun. 2, 2006

(86) PCT No.: PCT/JP2006/011054

§ 371 (c)(1), (2), (4) Date: Aug. 17, 2007

(87) PCT Pub. No.: WO2006/132133

PCT Pub. Date: Dec. 14, 2006

(65) Prior Publication Data

US 2008/0161589 A1    Jul. 3, 2008

(30) Foreign Application Priority Data

Jun. 6, 2005  (JP) .............................. 2005-165093
Feb. 3, 2006  (JP) .............................. 2006-026912

(51) Int. Cl.
C07F 7/02    (2006.01)
C11D 3/39    (2006.01)

(52) U.S. Cl. ................................. 556/173; 252/182.33

(58) Field of Classification Search ................ 556/173; 252/182.33
See application file for complete search history.

(56) References Cited

U.S. PATENT DOCUMENTS

| | | | |
|---|---|---|---|
| 4,322,513 A | 3/1982 | Wada et al. | |
| 4,324,873 A | 4/1982 | Wada et al. | |
| 6,794,038 B2 | 9/2004 | Matsushima | |
| 6,831,117 B2 | 12/2004 | Matsushima | |
| 6,921,782 B2 | 7/2005 | Matsushima | |
| 2004/0109943 A1 | 6/2004 | Matsushima et al. | |
| 2005/0107494 A1 | 5/2005 | Matsushima et al. | |

FOREIGN PATENT DOCUMENTS

| | | |
|---|---|---|
| CA | 2 293 067 A1 | 6/2000 |
| JP | A-56-004625 | 1/1981 |
| JP | A-05-313173 | 11/1993 |
| JP | A-2000-239472 | 9/2000 |
| JP | A-2001-137690 | 5/2001 |
| JP | A-2002-212537 | 7/2002 |
| JP | A-2002-363255 | 12/2002 |
| JP | A-2002-368047 | 12/2002 |
| JP | A-2003-013036 | 1/2003 |
| JP | A-2003-238656 | 8/2003 |
| JP | A-2006-013347 | 1/2006 |

*Primary Examiner*—Porfirio Nazario Gonzalez
(74) *Attorney, Agent, or Firm*—Oliff & Berridge, PLC

(57) ABSTRACT

An aluminum chelate-based latent curing agent capable of curing a thermosetting epoxy resin under the condition of relatively low temperature in a short period of time is provided. Furthermore, a method for manufacturing the latent curing agent is provided, in which the curing conditions of the aluminum chelate-based latent curing agent can be controlled relatively easily.

The aluminum chelate-based latent curing agent is prepared by reacting an aluminum chelate agent with a silsesquioxane type oxetane derivative in the presence of a water insoluble or poorly water-soluble cellulose ether, whereby latency properties are imparted thereto. This latent curing agent contains a coating layer composed of the water insoluble or poorly water-soluble cellulose ether. Preferably, the surface is treated with an isocyanate compound.

24 Claims, No Drawings

LATENT CURING AGENT

TECHNICAL FIELD

The present invention relates to an aluminum chelate-based latent curing agent capable of initiating curing of a thermosetting type composition at relatively low temperatures, a manufacturing method of the same, and a thermosetting type composition containing the same and having good storage stability.

BACKGROUND ART

Thermosetting type resin compositions such as epoxy resins have been widely employed as adhesive materials, molding materials, and the like. An imidazole-based latent curing agent has been employed as one of curing agents for such compositions. Such an imidazole-based latent curing agent does not exhibit curing ability under normal storage conditions and thus has been widely employed in order for a thermosetting epoxy resin composition to be used as a one-component type curable composition having good handleability and good storage stability. As a representative example of such an imidazole latent curing agent, a microcapsule-type imidazole latent curing agent is known in which the surface of imidazole compound particles having an ability to cure epoxy resin is coated with a cured epoxy resin material.

However, in order to initiate curing reaction, such a microcapsule-type imidazole latent curing agent must be pressurized and heated to 180° C. or higher since the coating thereof is relatively stable mechanically and also thermally. Therefore, a problem exists in that such a latent curing agent is unable to cope with recent low temperature curing type epoxy resin compositions.

Hence, as a latent curing agent exhibiting low-temperature fast-curing activity without using a toxic promoter such as antimony, a microcapsule-type aluminum chelate-based latent curing agent has been proposed (Patent Document 1). In this latent curing agent, fine particles of polyvinyl alcohol (child particles) are made to melt-adhere to the surface of particles of an aluminum chelate agent (parent particles) by means of a hybridization method to thereby form a polyvinyl alcohol coating layer on the surface of the parent particles. Here, the aluminum chelate agent co-operates with silanol (a silane coupling agent or the like) serving as a co-catalyst to generate a protonic acid and thus is capable of polymerizing cyclic ethers (epoxy compounds and oxetane compounds) through cationic ring-opening polymerization, and the above polyvinyl alcohol has a hydroxyl group which reacts with the aluminum chelate agent. In addition, another microcapsule-type aluminum chelate-based latent curing agent has been proposed (Patent Document 2). In this latent curing agent, fluororesin-based fine particles (child particles) not having a functional group capable of reacting with an aluminum chelate agent are made to electrostatically adhere to parent particles, and subsequently these fluororesin-based fine particles are fused by means of a hybridization method to thereby form a coating layer on the parent particles.

The detail of a curing step by means of the aluminum chelate-based latent curing agent is described in paragraphs [0007] to [0010] in the abovementioned Patent Document 1.

[Patent Document 1] Japanese Patent Application Laid-Open No. 2002-368047
[Patent Document 2] Japanese Patent Application Laid-Open No. 2002-363255

DISCLOSURE OF THE INVENTION

Problems To Be Solved By The Invention

However, as described in Patent Documents 1 and 2, when the aluminum chelate-based latent curing agent is microcapsulated by utilizing the hybridization method, the wall of the microcapsules is formed by impact-fusing the child particles on the parent particle or by friction fusing the electrostatically adhering child particles with each other. Therefore, a problem exists in that stable curing characteristics are not obtained since irregularity and unevenness are likely to be formed on the surface, and thus curing conditions are difficult to control. Furthermore, the polymerization initiation temperature of a thermosetting epoxy resin composition into which such a curing agent is mixed is too low relative to an exothermic peak in DSC (differential scanning calorimetry). Therefore, it is hard to say that latency properties are sufficient.

It is an object of the present invention to solve the above problems in conventional technology and to provide an aluminum chelate-based latent curing agent capable of curing a thermosetting resin through cationic polymerization under the condition of relatively low temperature in a short period of time. It is another object of the invention to provide a method for manufacturing the aluminum chelate-based latent curing agent, in which method curing conditions can be controlled relatively easily. It is another object of the invention to provide a thermosetting type resin composition containing the latent curing agent.

MEANS TO SOLVE THE PROBLEMS

The present inventors have found that the above object can be achieved by a material obtained as a precipitate which is formed by heating an aluminum chelate agent and a silsesquioxane type oxetane derivative in a nonaqueous solvent in the presence of a water insoluble or poorly water-soluble cellulose ether to thereby react the aluminum chelate agent with the oxetane derivative. Thus, the present invention has been completed.

Accordingly, the present invention provides an aluminum chelate-based latent curing agent wherein latency properties are imparted by reacting an aluminum chelate agent with a silsesquioxane type oxetane derivative in the presence of a water insoluble or poorly water-soluble cellulose ether. Specifically, the invention provides an aluminum chelate-based latent curing agent having a coating layer formed of the water insoluble or poorly water-soluble cellulose ether.

Moreover, the present invention provides a manufacturing method of the above latent curing agent. The latent curing agent is obtained as a precipitate which is formed by heating the aluminum chelate agent and the silsesquioxane type oxetane derivative in a nonaqueous solvent in the presence of the water insoluble or poorly water-soluble cellulose ether to thereby react the aluminum chelate agent with the silsesquioxane type oxetane derivative.

Furthermore, the present invention provides a thermosetting type composition containing the above latent curing agent, a silane coupling agent, and a thermosetting type compound.

ADVANTAGES OF THE INVENTION

The latent curing agent of the present invention is a latent curing agent to which latency properties are imparted by reacting an aluminum chelate agent with a silsesquioxane type oxetane derivative in the presence of a water insoluble or poorly water-soluble cellulose ether. The latency properties are considered to be achieved by the reason described below. That is, an oxetane ring in a silsesquioxane type oxetane derivative has higher nucleophilicity of ether oxygen than an oxirane ring and has excellent cationic polymerizability, and thus the silsesquioxane type oxetane derivative is polymerized through ring-opening by the action of the aluminum chelate agent. Furthermore, a silanol group may be formed when a part of alkoxysilyl groups in the polymer are subjected to hydrolysis by a very small amount of water in the polymerization system, or a silanol group may be present in the silsesquioxane type oxetane derivative from the outset. These silanol groups interact with the aluminum chelate agent, and therefore the aluminum chelate agent is combined and integrated with the polymerized material. Subsequently, the polymerization reaction is terminated, and the temperature of the solution of the polymerized material is lowered. Then, ethyl cellulose can no longer remain dissolved in the solution and forms a microcapsule wall around the polymerized material. Hence, latency properties are imparted to the nonaqueous type aluminum chelate-based curing agent. Therefore, the aluminum chelate agent, which is liquid at room temperatures, can also be employed as a latent curing agent.

Such a nonaqueous type aluminum chelate-based latent curing agent is capable of curing a thermosetting type compound such as an epoxy resin or an oxetane compound under the condition of relatively low temperature in a short period of time by melting the microcapsule wall. Furthermore, since this aluminum chelate-based latent curing agent can be manufactured in a nonaqueous solvent, the curing agent can be prevented from being inactivated, and the reduction of the curing performance can be suppressed.

BEST MODE FOR CARRYING OUT THE INVENTION

In the latent curing agent of the present invention, latency properties are imparted by reacting an aluminum chelate agent with a silsesquioxane type oxetane derivative in the presence of a water insoluble or poorly water-soluble cellulose ether. Since this latent curing agent employs an aluminum chelate agent which can realize low-temperature fast-curing properties, good low-temperature fast-curing properties can be imparted to a thermosetting type resin composition into which this latent curing agent is mixed. Moreover, since the aluminum chelate agent is coated with ethyl cellulose, even when this latent curing agent is mixed into a thermosetting type composition to form a one-component agent, the storage stability of the thermosetting type composition can be greatly improved.

The aluminum chelate-based latent curing agent of the present invention has a form of a microcapsule having a structure in which the periphery of a core formed by combining a polymer of the silsesquioxane type oxetane derivative with the aluminum chelate agent is coated with a shell of ethyl cellulose. When such microcapsules are aggregated, a structure may be formed in which a plurality of cores are interspersed in an ethyl cellulose matrix. Here, various polymers of the silsesquioxane type oxetane derivative polymers are obtained which have various degrees of polymerization (dimmers, oligomers, and higher polymers), depending on the charging amount of the aluminum chelate agent and the silsesquioxane type oxetane derivative, the reaction temperature condition, and the like. However, oligomers having a degree of polymerization of 10 to 100 are preferable in terms of particle diameter control.

Preferably, the shape of the latent curing agent of the present invention is spherical. In terms of curing properties and dispersion properties, the particle diameter of the latent curing agent is preferably 1 to 10 μm and more preferably 2 to 3 μm.

Furthermore, in the aluminum chelate-based latent curing agent of the present invention, when the amount of the silsesquioxane type oxetane derivative with respect to the amount of the aluminum chelate agent is too small, the capsulation reaction is slowed. Furthermore, when the amount is too large, the curing agent is solidified. Thus, the amount used is preferably 0.1 to 500 parts by weight, more preferably 1 to 500 parts by weight, and particularly preferably 10 to 500 parts by weight, with respect to 100 parts by weight of the aluminum chelate agent. When the amount of the water insoluble or poorly water-soluble cellulose ether with respect to the total amount of the aluminum chelate agent and the silsesquioxane type oxetane derivative is too small, powder is not formed. Furthermore, when the amount is too large, the curing properties deteriorate. Thus, the amount used is preferably 0.1 to 1,000 parts by weight, more preferably 0.5 to 500 parts by weight, and particularly preferably 1 to 500 parts by weight, with respect to 100 parts by weight of the total amount of the aluminum chelate agent and the silsesquioxane type oxetane derivative.

Examples of the aluminum chelate agent in the aluminum chelate-based latent curing agent of the present invention include a complex compound which is represented by formula (4) and in which three β-ketoenolate anions are coordinated to aluminum.

(Chemical formula 1)

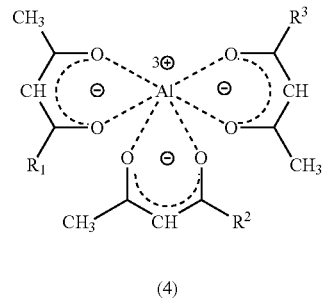

(4)

Here, $R^1$, $R^2$, and $R^3$ are independently an alkyl group or an alkoxyl group. Examples of the alkyl group include a methyl group and an ethyl group. Examples of the alkoxyl group include a methoxy group, an ethoxy group, and an oleyloxy group.

Specific examples of the aluminum chelate agent represented by the formula (4) include aluminum ethylacetoacetate diisopropylate (ALCH, Kawaken Fine Chemicals Co., Ltd.), aluminum trisethylacetoacetate (ALCH-TR, Kawaken Fine Chemicals Co., Ltd.), aluminum alkylacetoacetate diisopropylate (Aluminum chelate M, Kawaken Fine Chemicals Co., Ltd.), aluminum bisethylacetoacetate monoacetylacetonate (Aluminum chelate D, Kawaken Fine Chemicals Co., Ltd.), aluminum trisacetylacetonate (Aluminum chelate A(W), Kawaken Fine Chemicals Co., Ltd.), and alkylacetoacetate aluminum diisopropylate.

Examples of the silsesquioxane type oxetane derivative in the aluminum chelate-based latent curing agent of the present invention include a material containing preferably 95% or more of a compound (OX-SQ-H, TOAGOSEI CO., LTD.) which is represented by the following formula (1) and in which the silsesquioxane skeleton is substituted with at least one oxetanyl group having an oxetane ring. The compound represented by the formula (1) is normally a pale yellow viscous liquid having an average number molecular weight of 1,000 to 2,000. This compound is readily dissolved in a general organic solvent and can be easily mixed with epoxy resins and oxetanes. In addition to the silsesquioxane type oxetane derivative, other oxetane derivative (for example, a biphenyl type oxetane derivative; OXBP, UBE INDUSTRIES, LTD.) may also be employed within a range that does not impair the effects of the invention.

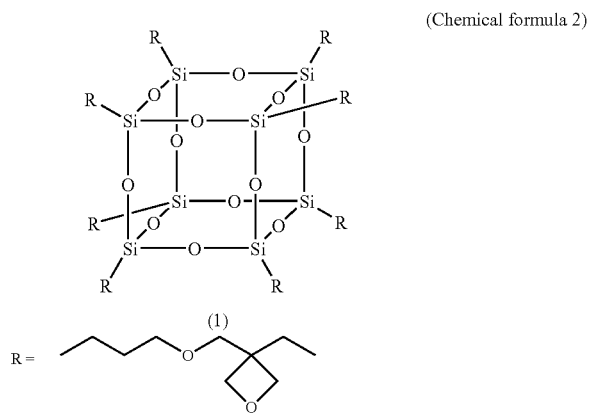

(Chemical formula 2)

The silsesquioxane type oxetane derivative of the formula (1) can be easily manufactured by condensing an alkoxysilyl group in an oxetanyl silane compound (OXT-610, TOAGOSEI CO., LTD., boiling temperature: 125 to 128° C./1 mmHg, viscosity: 7 to 8 mPa·s (25° C.)) represented by the formula (2) in the presence of an alkali or an acid/water. The compound of the formula (2) can be employed also as a silane coupling agent as described later.

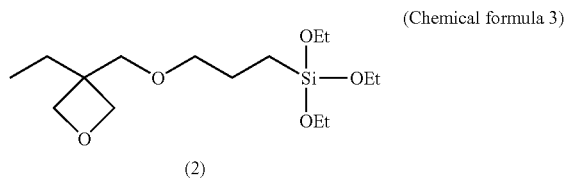

(Chemical formula 3)

Preferably, the water insoluble or poorly water-soluble cellulose ether employed in the aluminum chelate-based latent curing agent of the present invention has a solubility in purified water at 80° C. of 1.0 or less. Disadvantageously, when the solubility exceeds 1.0, it is difficult to dissolve the cellulose ether in an organic solvent. Examples of such a water insoluble or poorly water-soluble cellulose ether include ethyl cellulose and hydroxypropylmethyl cellulose. Of these, ethyl cellulose is preferable in terms of availability.

The aluminum chelate-based latent curing agent of the present invention can be obtained as a precipitate which is formed by heating the aluminum chelate agent and the silsesquioxane type oxetane derivative in a nonaqueous solvent in the presence of the water insoluble or poorly water-soluble cellulose ether to thereby react the aluminum chelate agent with the oxetane derivative and then by cooling the reaction system to, for example, room temperature.

As the nonaqueous solvent, a lower alkyl acetate such as ethyl acetate ester or an aromatic solvent such as toluene may be preferably employed. Heating temperature depends on the type and the like of the solvent and is normally 50 to 200° C. and preferably 80 to 200° C. Heating time is normally 1 to 3 hours and preferably 1 to 2 hours. The amount of the nonaqueous solvent used may be appropriately determined according to the solubility and the like of the water insoluble or poorly water-soluble cellulose ether.

After the reaction mixture is cooled, the precipitate generated is separated by filtration, washed with a poor solvent such as hexane, and dried under reduced pressure, whereby the aluminum chelate-based latent curing agent of the present invention can be obtained.

The aluminum chelate-based latent curing agent of the present invention is obtained as described above. In this case, by stirring the reaction system by use of a homogenizer (for example, IKA Japan K. K.), the latent curing agent is obtained as fine particles having a primary particle diameter of 0.5 to 10 μm in the reaction system. However, when the primary particles are removed from the reaction system, the particles tend to form secondary particles having a size of 0.5 to 100 μm. When an anisotropic conductive adhesive coating solution which employs such an aggregated relatively large size latent curing agent is applied to a substrate, the latent curing agent is caught by an application port of an applicator, and thus line-shaped patterns (application streaks) may be caused to which the coating solution is not sufficiently applied. The occurrence of such application streaks may be an obstacle to the realization of reliable anisotropic conduction connections. Hence, an operation is required in which the aggregated relatively large secondary particles of the aluminum chelate-based latent curing agent are crushed into the primary particles.

When crushing the particles, a hummer mill, a turbo mill, a roll mill, a jet mill, or the like may be employed. When a hummer mill, a turbo mill, or a roll mill is employed, the primary particles of the latent curing agent themselves are likely to be destroyed. Furthermore, when a jet mill is employed (see Japanese Patent Application Laid-Open No. 2001-137690), an apparatus becomes large, and thus a problem arises in that the crushing cost increases.

Therefore, the present inventors have continued studies in an attempt to impart, to the aluminum chelate-based latent curing agent, properties for resisting aggregation even when the latent curing agent is removed from the reaction system. The inventors have obtained an aluminum chelate-based latent curing agent obtained by heating and reacting the aluminum chelate agent and the silsesquioxane type oxetane derivative in the nonaqueous solvent in the presence of the water insoluble or poorly water-soluble cellulose ether and then by further reacting with an isocyanate compound. Consequently, the inventors have found that this aluminum chelate-based latent curing agent surely resists aggregation even when this curing agent is removed from the reaction system, and that, even when aggregation occurs, the aggregated curing agent can be broken into the primary particles under extremely mild conditions (for example, under settling conditions). Particularly, it has been found that when, after the reaction with the isocyanate compound, the resultant product is reacted with an epoxy compound or an oxetane compound, aggregation is further suppressed.

Moreover, the present inventors have obtained an aluminum chelate-based latent curing agent subjected to reaction with an epoxy or oxetane compound in combination with an isocyanate compound when the aluminum chelate agent and the silsesquioxane type oxetane derivative are heated and reacted in the nonaqueous solvent in the presence of the water insoluble or poorly water-soluble cellulose ether. The inventors have found that this aluminum chelate-based latent curing agent also surely resists aggregation even when this curing agent is removed from the reaction system, and that, even when aggregation occurs, the aggregated curing agent can be broken into the primary particles under extremely mild conditions (for example, under settling conditions).

Accordingly, as preferred embodiments, the present invention provides: (a) an aluminum chelate-based latent curing agent further subjected to reaction with an isocyanate compound after the latency properties are imparted; (b) an aluminum chelate-based latent curing agent further subjected to reaction with an epoxy compound or an oxetane compound after the reaction with the isocyanate compound; and (c) an aluminum chelate-based latent curing agent subjected to reaction with the epoxy or oxetane compound in combination with the isocyanate compound.

It should be noted that an isocyanate group in the isocyanate compound is considered to react with a hydroxyl group on the surface of the fine particles of the aluminum chelate-based latent curing agent. Therefore, the reaction with the isocyanate compound is considered to correspond to surface treatment of the aluminum chelate-based latent curing agent by means of the isocyanate compound. Furthermore, the epoxy compound and the oxetane compound are considered not to substantially react with an isocyanate group in the isocyanate compound. Therefore, the epoxy and oxetane compounds are considered to be cationic-polymerized by means of the aluminum chelate-based latent curing agent and fixed to the surface of the particles.

The isocyanate compound is a multifunctional isocyanate compound having two or more isocyanate groups in one molecule. Specific examples of the isocyanate compound include m-phenylene diisocyanate, p-phenylene diisocyanate, 2,4-tolylene diisocyanate, 2,6-tolylene diisocyanate, and naphthalene-1,4-diisocyanate. These may be employed after diluted with an organic solvent such as toluene.

When the amount of the isocyanate compound is too small, the effects of the reaction with the isocyanate compound are not expected. When the amount is too large, the reactivity of the curing agent is reduced. Therefore, the amount used is preferably 0.1 to 200 parts by weight and more preferably 0.1 to 100 parts by weight, with respect to 100 parts by weight of the aluminum chelate.

The epoxy compound is a multifunctional epoxy compound having two or more epoxy groups in one molecule. Specific examples of the epoxy compound include Bis-A type epoxy compounds such as Epikote 828 (product of Japan Epoxy Resins CO., Ltd.), Bis-F type epoxy compounds such as Epikote 806 (product of Japan Epoxy Resins CO., Ltd.), naphthalene type epoxy compounds such as HP-4032 (product of DAINIPPON INK AND CHEMICALS, INCORPORATED), and alicyclic epoxy compounds such as CEL2021P (product of DAICEL CHEMICAL INDUSTRIES, LTD.). Of these, the alicyclic epoxy compounds can be preferably employed in terms of high reactivity.

When the amount of the epoxy compound is too small, the effects of the reaction with the epoxy compound are not expected. When the amount is too large, the reactivity of the curing agent is reduced. Thus, the amount used is preferably 0.1 to 300 parts by weight and more preferably 0.1 to 200 parts by weight, with respect to 100 parts by weight of the aluminum chelate.

The oxetane compound is a multifunctional oxetane compound having two or more oxetanyl groups in one molecule. Specific examples of the oxetane compound include xylylene type oxetanes such as OTX-121 (product of TOAGOSEI CO., LTD.), silsesquioxane type oxetanes such as OX-SQ-H (product of TOAGOSEI CO., LTD.), ether type oxetanes such as OXT-221 (product of TOAGOSEI CO., LTD.), biphenyl type oxetanes such as ETERNACOLL OXBP (product of UBE INDUSTRIES, LTD.), phenolic novolac type oxetanes such as PNOX-723 (product of TOAGOSEI CO., LTD.), and silicate type oxetanes such as OX-SC (product of TOAGOSEI CO., LTD.). Of these, the xylylene type oxetanes, the biphenyl type oxetanes, and the phenolic novolac type oxetanes can be preferably employed in terms of high heat resistance of a cured material.

When the amount of the oxetane compound is too small, the effects of the reaction with the oxetane compound are not expected. When the amount is too large, the reactivity of the curing agent is reduced. Thus, the amount used is preferably 0.1 to 300 parts by weight and more preferably 0.1 to 200 parts by weight, with respect to 100 parts by weight of the aluminum chelate.

When the reaction with the isocyanate compound and the epoxy or oxetane compound described above are carried out, the reaction may be carried out at the reaction temperature at which the aluminum chelate agent and the silsesquioxane type oxetane derivative are heated and reacted in the nonaqueous solvent in the presence of the water insoluble or poorly water-soluble cellulose ether.

According to the manufacturing method of the present invention as described above, the curing characteristics of the aluminum chelate-based latent curing agent can be controlled by changing the type and the amount of the silsesquioxane type oxetane derivative used and the water insoluble or poorly water-soluble cellulose ether used, the type and the amount of the aluminum chelate agent used, and the reaction conditions. For example, when the reaction temperature is lowered, the curing temperature can be lowered. On the other hand, when the reaction temperature is raised, the curing temperature can be raised.

The aluminum chelate-based latent curing agent of the present invention can be used for the same applications as those for a conventional imidazole-based latent curing agent. Preferably, by using the present latent curing agent in combination with a silane coupling agent and a thermosetting type compound, a thermosetting type composition having low-temperature fast-curing properties can be provided.

When the content of the aluminum chelate-based latent curing agent in a thermosetting type composition is too small, the thermosetting type composition is not satisfactorily cured. When the content is too large, the resin characteristics (for example, flexibility) of the cured material of the composition are deteriorated. Therefore, the content thereof is 1 to 30 parts by weight and preferably 1 to 20 parts by weight, with respect to 100 parts by weight of the thermosetting type compound.

As described in paragraphs [0010] to [0014] in Japanese Patent Application Laid-Open No. 2002-368047, a silane coupling agent has a function of initiating cationic polymerization of a thermosetting resin (for example, a thermosetting epoxy resin) by co-operating with an aluminum chelate agent. Also, the silane coupling agent is considered to have a function of stabilizing the reaction system by capping an unstable hydroxyl group which remains in the water insoluble or poorly water-soluble cellulose ether after the curing reaction and can serve as a catalyst poison. Such a silane coupling agent has one to three lower alkoxy groups in the molecule and may have, in the molecule, a group having reactivity with a functional group in a thermosetting resin. Examples of such a group include a vinyl group, a styryl group, an acryloyloxy group, a methacryloyloxy group, an epoxy group, an amino group, and a mercapto group. Of these, an alicyclic epoxy-based silane coupling agent is preferable. Furthermore, since the latent curing agent of the present invention is a cationic type curing agent, a coupling agent having an amino group or a mercapto group can be used when the amino group or the mercapto group does not substantially capture cation species generated. Also, preferably, the alicyclic epoxy-based silane coupling agent is used in combination with an ethoxysilyl group-containing silane coupling agent. In this case, an exothermic onset temperature and a rising peak can be balanced.

Specific examples of such a silane coupling agent include vinyl-tris (2-methoxyethoxy) silane, vinyltriethoxysilane, vinyltrimethoxysilane, 3-styryltrimethoxysilane, 3-methacryloxypropyltrimethoxysilane, 3-acryloxypropyltrimethoxysilane, 3-glycidoxypropyltrimethoxysilane, 3-glycidoxypropylmethyldiethoxysilane, N-2-(aminoethyl)-3-aminopropyltrimethoxysilane, N-2-(aminoethyl)-3-aminopropylmethyldimethoxysilane, 3-aminopropyltriethoxysilane, N-phenyl-3-aminopropyltrimethoxysilane, 3-mercaptopropyltrimethoxysilane, and 3-chloropropyltrimethoxysilane. Preferred examples of the alicyclic epoxy-based silane coupling agent include 2-(3,4-epoxycyclohexyl) ethyltrimethoxysilane represented by the formula (3).

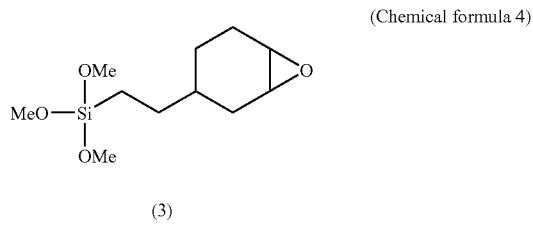

(Chemical formula 4)

(3)

When the content of the silane coupling agent in the thermosetting type composition is too small, this composition exhibits low curing characteristics. Furthermore, when the content is too large, the resin characteristics (for example, storage stability) of the cured material of the composition deteriorate. Therefore, the content thereof is preferably 1 to 1,000 parts by weight and preferably 50 to 500 parts by weight, with respect to 100 parts by weight of the aluminum chelate-based latent curing agent.

As the thermosetting type compound, a thermosetting type epoxy resin, a thermosetting type urea resin, a thermosetting type melamine resin, a thermosetting type phenolic resin, an oxetane compound, or the like may be employed. Of these, the thermosetting type epoxy resin can be preferably employed in view of good adhesion strength after curing.

Such a thermosetting type epoxy resin may be liquid or solid, and a thermosetting type epoxy resin having an epoxy equivalent weight of normally about 100 to about 4,000 and having two or more epoxy groups in the molecule is preferable. For example, a bisphenol A type epoxy compound, a phenolic novolak type epoxy compound, a cresol novolak type epoxy compound, an ester type epoxy compound, an alicyclic epoxy compound, and the like can be preferably employed. Furthermore, these compounds include monomers and oligomers. Of these, the alicyclic epoxy compound such as CEL2021P (product of DAICEL CHEMICAL INDUSTRIES, LTD.) can be preferably employed in terms of high reactivity.

The oxetane compound may be liquid or solid, and an oxetane compound having two or more oxcetanyl groups in the molecule is preferable. For example, OXT-121, OXT-221, OX-SQ-H (products of TOAGOSEI CO., LTD.) can be preferably employed. Furthermore, these compounds include monomers and oligomers. Of these, OXT-221, OX-SQ-H, and the like can be preferably employed in terms of reactivity and low concentrations of ionic impurities.

The thermosetting type composition of the present invention can be manufactured by uniformly mixing and stirring, according to a routine method, the aluminum chelate-based latent curing agent, the silane coupling agent, the thermosetting type compound, and other additives added in accordance with need.

Although the thus-obtained thermosetting type composition of the present invention is a one-component type, this composition has excellent storage stability since the latency properties are imparted to the aluminum chelate-based curing agent. Furthermore, the latent curing agent is co-operated with the silane coupling agent, whereby the thermosetting type compound can be cationic-polymerized through low-temperature fast-curing.

EXAMPLES

Hereinafter, the present invention will be specifically described by way of examples. Group A of Examples and Comparative Examples is an example for evaluating a shell ratio and latency properties of the curing agent. Group B of Examples is an example for evaluating the primary particle diameter (the presence and absence of aggregation) and the latency properties of the curing agent particles affected by treatment with the isocyanate compound.

Example A1

Into a three necked flask made of Teflon (registered trademark) and equipped with a cooling tube were charged 159.7 g of kerosene, 10 g of a 10% ethyl acetate solution of ethyl cellulose, 9.1 g of a 66% toluene solution of an aluminum chelate agent (ethylacetoacetate aluminum diisopropylate; ALCH, Kawaken Fine Chemicals Co., Ltd.), 21.2 g of a 66% toluene solution of a silsesquioxane type oxetane derivative (OX-SQ-H, TOAGOSEI CO., LTD.), and 0.04 g of a silane coupling agent (A-187, Nippon Unicar Company Limited). The mixture was heated using a mantle heater, and the heating was terminated when the temperature of the reaction mixture reached 120° C. Then, the reaction mixture was cooled to room temperature by use of an ice bath. As a result, a precipitate was formed. Subsequently, the reaction mixture was filtrated to collect the precipitate. The precipitate was washed with hexane three times and was dried under reduced pressure, thereby obtaining 9.9 g of a white solid as an aluminum chelate-based latent curing agent.

Example A2

Example A1 was repeated except that the silane coupling agent was not employed, thereby obtaining 10.0 g of a white solid as an aluminum chelate-based latent curing agent.

Example A3

Example 2 was repeated except that 10.6 g in place of 21.2 g of a 66% toluene solution of the silsesquioxane type oxetane derivative (OX-SQ-H, TOAGOSEI CO., LTD.) was used, and that 10.6 g of 66% toluene solution of biphenyl type oxetane (OXBP, UBE INDUSTRIES, LTD.) was further used in combination with the oxetane derivative, thereby obtaining 4.4 g of a white solid as an aluminum chelate-based latent curing agent.

Comparative Example A1

Example A1 was repeated except that ethyl cellulose was not employed, thereby obtaining 2.6 g of a white solid as an aluminum chelate-based curing agent.

Example A4

Into a three necked flask made of Teflon (registered trademark) and equipped with a cooling tube were charged 159.7 g of kerosene, 80 g of a 10% ethyl acetate solution of ethyl cellulose, 9.1 g of a 66% toluene solution of an aluminum chelate agent (ethylacetoacetate aluminum diisopropylate; ALCH, Kawaken Fine Chemicals Co., Ltd.), and 21.2 g of a 66% toluene solution of a silsesquioxane type oxetane derivative (OX-SQ-H, TOAGOSEI CO., LTD.). The mixture was heated using a mantle heater, and the heating was terminated when the temperature of the reaction mixture reached 120° C. Then, the reaction mixture was cooled to room temperature by use of an ice bath. As a result, a precipitate was formed. Subsequently, the reaction mixture was filtrated to collect the precipitate. The precipitate was washed with hexane three times and was dried under reduced pressure, thereby obtaining 26.1 g (yield: 93%) of a white solid as an aluminum chelate-based latent curing agent.

Example A5

Example A4 was repeated except that the amount of 10% ethyl acetate solution of ethyl cellulose was changed to 60 g, thereby obtaining 24.5 g (yield: 94%) of a white solid as an aluminum chelate-based latent curing agent.

Example A6

Example A4 was repeated except that the amount of 10% ethyl acetate solution of ethyl cellulose was changed to 40 g, thereby obtaining 19.7 g (yield: 82%) of a white solid as an aluminum chelate-based latent curing agent.

Example A7

Example A4 was repeated except that the amount of 10% ethyl acetate solution of ethyl cellulose was changed to 20 g, thereby obtaining 11.8 g (yield: 54%) of a white solid as an aluminum chelate-based latent curing agent.

Example A8

Example A4 was repeated except that the amount of 10% ethyl acetate solution of ethyl cellulose was changed to 10 g (i.e., completely the same procedure as in Example A2 was repeated), thereby obtaining 10.0 g (yield: 50%) of a white solid as an aluminum chelate-based latent curing agent.

Comparative Example A2

Example A4 was repeated except that ethyl cellulose was not used, thereby obtaining 2.5 g of a white solid as an aluminum chelate-based curing agent.

Comparative Example A3

Into a three necked flask made of Teflon (registered trademark) and equipped with a cooling tube were charged 172.5 g of kerosene, 10 g of a 10% ethyl acetate solution of ethyl cellulose, 9.1 g of a 66% toluene solution of an aluminum chelate agent (ethylacetoacetate aluminum diisopropylate; ALCH, Kawaken Fine Chemicals Co., Ltd.), and 8.4 g of a 66% toluene solution of an alicyclic epoxy resin (CEL2021P, DAICEL CHEMICAL INDUSTRIES, LTD.). The mixture was heated using a mantle heater, and the heating was terminated when the temperature of the reaction mixture reached 180° C. Then, the reaction mixture was cooled to room temperature by use of an ice bath. As a result, a precipitate was formed. Subsequently, the reaction mixture was filtrated to collect the precipitate. The precipitate was washed with hexane three times and was dried under reduced pressure, thereby obtaining 1.1 g (yield: 8.6%) of a white solid as an aluminum chelate-based curing agent.

Example A9

Into a three necked flask made of Teflon (registered trademark) and equipped with a cooling tube were charged 167.3 g of kerosene, 10 g of a 10% ethyl acetate solution of ethyl cellulose, 4.2 g of a 66% toluene solution of an aluminum chelate agent (ethylacetoacetate aluminum diisopropylate; ALCH, Kawaken Fine Chemicals Co., Ltd.), and 9.4 g of a 66% toluene solution of a silsesquioxane type oxetane derivative (OX-SQ-H, TOAGOSEI CO., LTD.). The mixture was heated using a mantle heater, and the heating was terminated when the temperature of the reaction mixture reached 180° C. Then, the reaction mixture was cooled to room temperature by use of an ice bath. As a result, a precipitate was formed. Subsequently, the reaction mixture was filtrated to collect the precipitate. The precipitate was washed with hexane three times and was dried under reduced pressure, thereby obtaining 9.8 g (yield: 61%) of a white solid as an aluminum chelate-based curing agent.

(Evaluation)

Thermosetting type compositions described below were prepared, and thermal analysis was preformed by use of a differential scanning calorimetry (DSC) apparatus (DSC-60, product of Shimadzu Corporation) to determine an exothermic onset temperature (° C.), an exothermic peak temperature (° C.), and a gross calorific value (j/g). A shell ratio (%) was calculated as the weight percent of ethyl cellulose. The results obtained are shown in Table 1.

(Curing Agent for Examples A1 to A3 and Comparative Example A1)

By use of a stirrer, 3.3 g of an alicyclic epoxy resin (CEL2021P, DAICEL CHEMICAL INDUSTRIES, LTD.), 0.2 g of the curing agent, and 0.8 g of a silane coupling agent (A-187, Nippon Unicar Company Limited) were uniformly mixed, thereby obtaining a thermosetting type composition.

(Curing Agent for Examples A4 to A8 and Comparative Example A2)

By use of a stirrer, 3.3 g of an oxetane derivative (DOX, TOAGOSEI CO., LTD.), 0.2 g of the curing agent, and 0.8 g of a silane coupling agent (A-187, Nippon Unicar Company Limited) were uniformly mixed, thereby obtaining a thermosetting type composition.

Comparative Example A3 and Example A9

By use of a stirrer, 3.3 g of an oxetane derivative (DOX, TOAGOSEI CO., LTD.), 0.2 g of the curing agent, and 0.8 g of a silane coupling agent (1:1 mixture of KBE403 (Shin-Etsu Chemical Co., Ltd.) and KBM303 (Shin-Etsu Chemical Co., Ltd.)) were uniformly mixed, thereby obtaining a thermosetting type composition.

TABLE 1

| Curing agent used | Shell ratio (%) | Exothermic onset temp (° C.) | Exothermic peak temp (° C.) | Gross calorific value (J/g) |
|---|---|---|---|---|
| Example A1 | 4.8 | 65.0 | 97.5 | 407.1 |
| Example A2 | 4.8 | 49.6 | 92.3 | 348.9 |
| Example A3 | 4.8 | 35.2 | 90.2 | 468.8 |
| Comparative Example A1 | 0 | Cured in 5 minutes at room temperature | | |
| Example A4 | 28.6 | 77.1 | 96.3 | 259.4 |
| Example A5 | 23.1 | 76.0 | 93.2 | 414.9 |
| Example A6 | 16.7 | 73.5 | 93.0 | 293.2 |
| Example A7 | 9.1 | 68.5 | 106.7 | 386.4 |
| Example A8 | 4.8 | 67.6 | 117.2 | 410.1 |
| Comparative Example A2 | 0 | 50.8 | 87.1 | 488.3 |
| Comparative Example A3 | 8.0 | 63.0 | 101.2 | 427.6 |
| Example A9 | 6.3 | 69.6 | 100.2 | 431.9 |

As can be seen from the results of Examples A1 to A3 and Comparative Example A1 in Table 1, latency properties can be imparted to aluminum chelate-based curing agents by encapsulating with ethyl cellulose. In addition, when the shell ratio is constant, the difference between the exothermic onset temperature and the exothermic peak temperature can be reduced by adding the silane coupling agent.

As can be seen from the results of Examples A4 to A8 and Comparative Example A2 in Table 1, by increasing the amount of ethyl cellulose used, the exothermic onset temperature can be raised while the exothermic peak temperature remains constant. That is, the exothermic peak can be sharpened.

As can be seen from the results of Comparative Example A3 and Example A9 in Table 1, even when the oxetane compound was used in place of the thermosetting type epoxy resin, the effects of the present invention can also be obtained.

Example B1

Into a three necked flask made of Teflon (registered trademark) and equipped with a cooling tube and a homogenizer (IKA Japan K. K.) were charged 258.1 g of kerosene, 15 g of ethyl cellulose, 9.1 g of a 66% toluene solution of an aluminum chelate agent (ethylacetoacetate aluminum diisopropylate; ALCH, Kawaken Fine Chemicals Co., Ltd.), and 9.4 g of a 66% toluene solution of a silsesquioxane type oxetane derivative (OX-SQ-H, TOAGOSEI CO., LTD.). The mixture was heated using a mantle heater. When the temperature of the reaction mixture reached 160° C., 15 g of an isocyanate compound (Colonate L45E, product of NIPPON POLYURETHANE INDUSTRY CO., LTD) was added to the reaction mixture, and the reaction mixture was stirred for one hour while being heated at 160° C. After one hour, the reaction mixture was cooled to room temperature by use of an ice bath. As a result, a precipitate was formed. Subsequently, the reaction mixture was filtrated to collect the precipitate. The precipitate was washed with heptane three times and was dried under reduced pressure, thereby obtaining 26.1 g (yield: 77%) of a pale yellow solid powder as an aluminum chelate-based latent curing agent.

Example B2

Into a three necked flask made of Teflon (registered trademark) and equipped with a cooling tube and a homogenizer (IKA Japan K. K.) were charged 258.1 g of kerosene, 15 g of ethyl cellulose, 9.1 g of a 66% toluene solution of an aluminum chelate agent (ethylacetoacetate aluminum diisopropylate; ALCH, Kawaken Fine Chemicals Co., Ltd.), and 9.4 g of a 66% toluene solution of a silsesquioxane type oxetane derivative (OX-SQ-H, TOAGOSEI CO., LTD.). The mixture was heated using a mantle heater. When the temperature of the reaction mixture reached 160° C., to the reaction mixture was added a mixture of 5 g of an isocyanate compound (Colonate L45E, product of NIPPON POLYURETHANE INDUSTRY CO., LTD) and 4.2 g of a 66% toluene solution of an alicyclic epoxy compound (CEL2021P, DAICEL CHEMICAL INDUSTRIES, LTD.). The reaction mixture was stirred for one hour while being heated at 160° C. After one hour, the reaction mixture was cooled to room temperature by use of an ice bath. As a result, a precipitate was formed. Subsequently, the reaction mixture was filtrated to collect the precipitate. The precipitate was washed with heptane three times and was dried under reduced pressure, thereby obtaining 30.4 g (yield: 94%) of a pale yellow solid powder as an aluminum chelate-based latent curing agent.

Example B3

Into a three necked flask made of Teflon (registered trademark) and equipped with a cooling tube and a homogenizer (IKA Japan K. K.) were charged 258.1 g of kerosene, 15 g of S ethyl cellulose, 9.1 g of a 66% toluene solution of an aluminum chelate agent (ethylacetoacetate aluminum diisopropylate; ALCH, Kawaken Fine Chemicals Co., Ltd.), and 9.4 g of a 66% toluene solution of a silsesquioxane type oxetane derivative (OX-SQ-H, TOAGOSEI CO., LTD.). The mixture was heated using a mantle heater. When the temperature of the reaction mixture reached 120° C., 5 g of an isocyanate compound (Colonate L45E, product of NIPPON POLYURETHANE INDUSTRY CO., LTD) was added to the reaction mixture, and the reaction mixture was stirred at 120° C. for 30 minutes. Furthermore, 6.7 g of a 66% toluene solution of novolak type oxetane (PNOX723, TOAGOSEI CO., LTD.) was added, and the reaction mixture was stirred at 120° C. for 30 minutes. Subsequently, the reaction mixture was cooled to room temperature by use of an ice bath. As a result, a precipitate was formed. Subsequently, the reaction mixture was filtrated to collect the precipitate. The precipitate was washed with heptane three times and was dried under reduced pressure, thereby obtaining 28.3 g (yield: 84%) of a pale yellow solid powder as an aluminum chelate-based latent curing agent.

Example B4

Into a three necked flask made of Teflon (registered trademark) and equipped with a cooling tube and a homogenizer (IKA Japan K. K.) were charged 258.1 g of kerosene, 15 g of ethyl cellulose, 9.1 g of a 66% toluene solution of an aluminum chelate agent (ethylacetoacetate aluminum diisopropylate; ALCH, Kawaken Fine Chemicals Co., Ltd.), and 9.4 g of a 66% toluene solution of a silsesquioxane type oxetane derivative (OX-SQ-H, TOAGOSEI CO., LTD.). The mixture was heated using a mantle heater. When the temperature of the reaction mixture reached 160° C., the reaction mixture was cooled to room temperature by use of an ice bath. As a result, a precipitate was formed. Subsequently, the reaction mixture was filtrated to collect the precipitate. The precipitate was washed with heptane three times and was dried under reduced pressure, thereby obtaining 20.4 g (yield: 75%) of a pale yellow solid powder as an aluminum chelate-based latent curing agent.

Example B5

Into a three necked flask made of Teflon (registered trademark) and equipped with a cooling tube and a homogenizer (IKA Japan K. K.) were charged 258.1 g of kerosene, 15 g of ethyl cellulose, 9.1 g of a 66% toluene solution of an aluminum chelate agent (ethylacetoacetate aluminum diisopropylate; ALCH, Kawaken Fine Chemicals Co., Ltd.), and 9.4 g of a 66% toluene solution of a silsesquioxane type oxetane derivative (OX-SQ-H, TOAGOSEI CO., LTD.). The mixture was heated using a mantle heater. When the temperature of the reaction mixture reached 120° C., 4.2 g of a 66% toluene solution of an alicyclic epoxy compound (CEL2021P, DAICEL CHEMICAL INDUSTRIES, LTD.) was added to the reaction mixture, and the reaction mixture was stirred at 120° C. for one hour. After one hour, the reaction mixture was cooled to room temperature by use of an ice bath. As a result, a precipitate was formed. Subsequently, the reaction mixture was filtrated to collect the precipitate. The precipitate was washed with heptane three times and was dried under reduced pressure, thereby obtaining 24.0 g (yield: 80%) of a pale yellow solid powder as an aluminum chelate-based latent curing agent.

(Evaluation)

A thermosetting type composition described below was prepared, and thermal analysis was preformed by use of a differential scanning calorimetry (DSC) apparatus (DSC-60, product of Shimadzu Corporation) to determine an exothermic onset temperature (° C.), an exothermic peak temperature (° C.) and a gross calorific value (j/g). The average particle diameter of the primary particles was observed by means of a particle image analyzer (SYSMEX CORPORATION). In addition, the degree of aggregation of the curing agent just after synthesis-purification was visually observed and evaluated. The results obtained are shown in Table 2.

(Curing Agent for Examples B1 to B5)

By use of a stirrer, 3.3 g of an oxetane derivative (DOX, TOAGOSEI CO., LTD.), 0.2 g of the curing agent of Examples B1 to B5, and 0.8 g of a silane coupling agent (1:1 mixture of KBE403 (Shin-Etsu Chemical Co., Ltd.) and KBM303 (Shin-Etsu Chemical Co., Ltd.)) were uniformly mixed, thereby obtaining a thermosetting type composition.

As seen from the results in Table 2, latency properties were observed in each of the curing agents of Examples B1 to B5. In Examples B1 to B3 in which the reaction with the isocyanate compound was performed, the exothermic onset temperature was higher than those in Examples B4 and B5 in which the reaction with the isocyanate compound was not performed. Furthermore, aggregation was not observed, and the average diameter of the primary particles was very small, 2.5 to 3.5 μm. Moreover, in the curing agent of Example B2 which agent was subjected to the reaction with the alicyclic epoxy compound in addition to the isocyanate compound, the gross calorific value increased, and thus this curing agent is preferable in terms of reactivity. Furthermore, in the curing agent of Example B3 which agent was subjected to the reaction with the oxetane compound, the exothermic peak temperature was increased, and the heat resistance was found to be improved.

INDUSTRIAL APPLICABILITY

The aluminum chelate-based latent curing agent of the present invention is capable of curing a thermosetting composition under the condition of relatively low temperature in a short period of time and thus is useful as an adhesion material employed for electronic materials and capable of being cured at low temperature or other materials.

The invention claimed is:

1. An aluminum chelate-based latent curing agent to which latency properties are imparted by reacting an aluminum chelate agent with a silsesquioxane type oxetane derivative in the presence of a water insoluble or poorly water-soluble cellulose ether.

2. The aluminum chelate-based latent curing agent according to claim 1, containing a coating layer composed of a water insoluble or poorly water-soluble cellulose ether.

3. The aluminum chelate-based latent curing agent according to claim 1, wherein the aluminum chelate agent is a complex compound in which three β-ketoenolate anions are coordinated to aluminum.

4. The aluminum chelate-based latent curing agent according to claim 1, wherein the aluminum chelate agent is aluminum ethylacetoacetate diisopropylate, aluminum trisethylacetoacetate, aluminum alkylacetoacetate diisopropylate, aluminum bisethylacetoacetate monoacetylacetonate, or aluminum trisacetylacetonate.

5. The aluminum chelate-based latent curing agent according to claim 1, wherein the aluminum chelate agent is aluminum ethylacetoacetate diisopropylate.

6. The aluminum chelate-based latent curing agent according to claim 1, wherein the silsesquioxane type oxetane derivative contains oxetanyl silsesquioxane represented by the following formula (1):

TABLE 2

| Curing agent used | Aggregation | Average diameter of primary particle (μm) | Exothermic onset temp (° C.) | Exothermic peak temp (° C.) | Gross calorific value (J/g) |
| --- | --- | --- | --- | --- | --- |
| Example B1 | No | 2.5 | 90.6 | 112.6 | 256.0 |
| Example B2 | No | 3.0 | 93.5 | 115.9 | 342.0 |
| Example B3 | No | 3.5 | 93.0 | 134.5 | 346.9 |
| Example B4 | Yes | 12.6 | 65.5 | 105.7 | 398.7 |
| Example B5 | Slight | 9.8 | 70.8 | 111.5 | 358.1 |

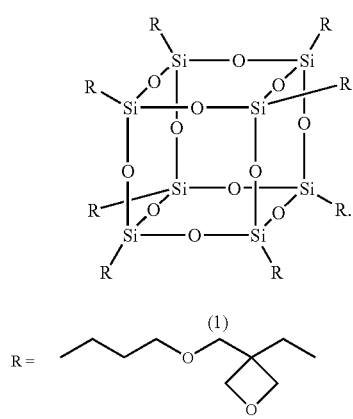

(Chemical formula 1)

7. The aluminum chelate-based latent curing agent according to claim 1, wherein the water insoluble or poorly water-soluble cellulose ether is ethyl cellulose.

8. The aluminum chelate-based latent curing agent according to claim 1, containing 0.1 to 500 parts by weight of the silsesquioxane type oxetane derivative with respect to 100 parts by weight of the aluminum chelate agent and 0.1 to 1,000 parts by weight of the water insoluble or poorly water-soluble cellulose ether with respect to 100 parts by weight of the total of the aluminum chelate agent and the silsesquioxane type oxetane derivative.

9. The aluminum chelate-based latent curing agent according to claim 1, wherein the aluminum chelate-based latent curing agent is subjected to further reaction with an isocyanate compound after the latency properties are imparted.

10. The aluminum chelate-based latent curing agent according to claim 9, wherein the aluminum chelate-based latent curing agent is subjected to further reaction with an epoxy compound or an oxetane compound after the reaction with the isocyanate compound.

11. The aluminum chelate-based latent curing agent according to claim 9, wherein the aluminum chelate-based latent curing agent is subjected to reaction with an epoxy compound or an oxetane compound in combination with the isocyanate compound.

12. The aluminum chelate-based latent curing agent according to claim 9, wherein the isocyanate is m-phenylene diisocyanate, p-phenylene diisocyanate, 2,4-tolylene diisocyanate, 2,6-tolylene diisocyanate, or naphthalene-1,4-diisocyanate.

13. The aluminum chelate-based latent curing agent according to claim 10, wherein the epoxy compound is a Bis-A type epoxy compound, a Bis-F type epoxy compound, a naphthalene type epoxy compound, or an alicyclic epoxy compound.

14. The aluminum chelate-based latent curing agent according to claim 10, wherein the oxetane compound is a xylylene type oxetane, a silsesquioxane type oxetane, an ether type oxetane, a biphenyl type oxetane, a phenolic novolac type oxetane, or a silicate type oxetane.

15. A manufacturing method of the aluminum chelate-based latent curing agent according to claim 1, comprising obtaining the aluminum chelate-based latent curing agent as a precipitate by heating an aluminum chelate agent and a silsesquioxane type oxetane derivative in a nonaqueous solvent in the presence of a water insoluble or poorly water-soluble cellulose ether to thereby react the aluminum chelate agent with the silsesquioxane type oxetane derivative.

16. The manufacturing method according to claim 15, wherein the nonaqueous solvent contains a lower alkyl acetate.

17. The manufacturing method according to claim 15, wherein a heating temperature is 80 to 200° C.

18. A thermosetting type composition containing the aluminum chelate-based latent curing agent according to claim 1, a silane coupling agent, and a thermosetting type compound.

19. The thermosetting type composition according to claim 18, wherein the thermosetting type compound is an alicyclic epoxy compound.

20. The thermosetting type composition according to claim 18, wherein the thermosetting type compound is an oxetane compound.

21. The thermosetting type composition according to claim 18, wherein the silane coupling agent is an oxetane-based silane coupling agent.

22. The thermosetting type composition according to claim 21, wherein the oxetane-based silane coupling agent is represented by the following formula (2):

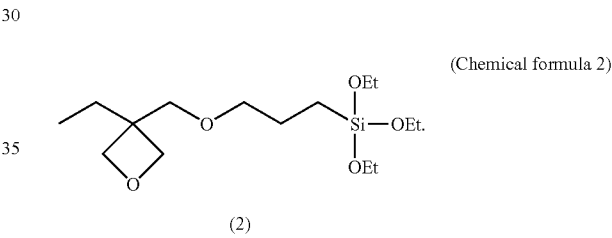

(Chemical formula 2)

23. The thermosetting type composition according to claim 18, wherein the silane coupling agent contains an alicyclic epoxy-based silane coupling agent and a silane coupling agent containing an ethoxysilyl group.

24. The thermosetting type composition according to claim 23, wherein the alicyclic epoxy-based silane coupling agent is 2-(3,4-epoxycyclohexyl) ethyltrimethoxysilane represented by the formula (3):

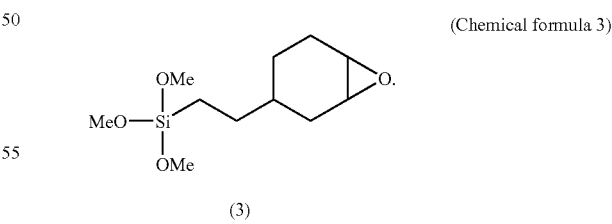

(Chemical formula 3)

* * * * *